United States Patent
Grady

[11] Patent Number: 5,408,521
[45] Date of Patent: Apr. 18, 1995

[54] ANGIOGRAPHIC X-RAY SYSTEM WITH 360 DEGREE SCANNING

[76] Inventor: John K. Grady, XRE Corporation, 300 Foster St., Littleton, Mass. 01460

[21] Appl. No.: 868,481

[22] Filed: Apr. 14, 1992

[51] Int. Cl.[6] .............................. H05G 1/64
[52] U.S. Cl. .......................... 378/96; 378/4; 378/15; 378/901
[58] Field of Search .............. 378/99, 95, 96, 98, 378/62, 155, 165, 207, 901, 4, 15; 358/111; 128/653

[56] References Cited

U.S. PATENT DOCUMENTS

| | | | |
|---|---|---|---|
| 4,144,457 | 3/1979 | Albert | 378/9 |
| 4,309,615 | 1/1982 | Kowalski | 378/9 |
| 4,382,184 | 5/1983 | Wernikoff | 378/37 |
| 4,433,380 | 2/1984 | Abele et al. | 378/901 |
| 4,559,557 | 12/1985 | Keyes et al. | 378/99 |
| 4,669,105 | 5/1987 | Fenster et al. | 378/146 |
| 4,672,651 | 6/1987 | Horiba et al. | 378/901 |
| 4,878,115 | 10/1989 | Elion | 378/95 |
| 4,887,604 | 12/1989 | Shefer et al. | 378/62 |
| 4,995,064 | 2/1991 | Wilson et al. | 378/4 |
| 5,095,501 | 3/1992 | Kobayashi | 378/196 |
| 5,218,623 | 6/1993 | Toki et al. | 378/4 |

Primary Examiner—Georgia Y. Epps
Assistant Examiner—Kim-Kwok Chu
Attorney, Agent, or Firm—James H. Grover

[57] ABSTRACT

An X-ray system scans the vascular portion of a human patient by a series of rapidly pulsed exposures from an X-ray tube rotated continuously through 360 degrees around the patient. The tube emits a cone-shaped beam through the patient to a receptor which generates a corresponding series of two-dimensional video images of the patient from successive angles.

13 Claims, 1 Drawing Sheet

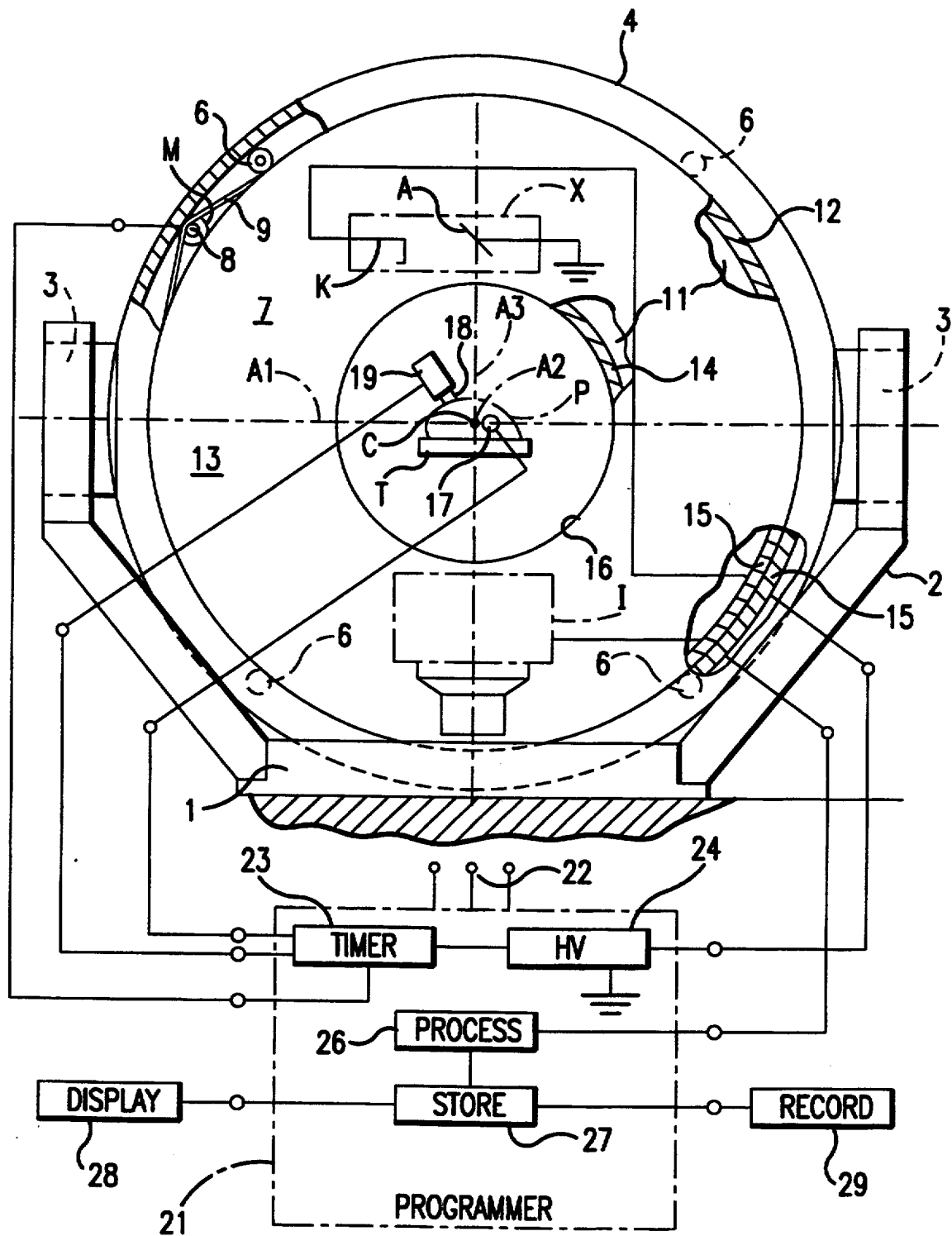

ANGIOGRAPHIC X-RAY SYSTEM WITH 360 DEGREE SCANNING

BACKGROUND OF THE INVENTION

Although it is desirable, in angiographic examination of human vascular portions injected with a contrast medium, to scan with an X-ray beam rotating around the patient so as to produce a series of X-ray images at successive angles, a remaining problem is that available rotational X-ray scanners do not rotate fast enough to complete a substantial angular scan, e.g. up to 180 degrees, during the short period while the contrast medium remains in the vascular body portion under examination, e.g. 3 seconds. Extending the time and the amount of injected contrast medium increases the risk to the patient from the medium's toxicity. Available X-ray systems suitable for angiographic examination are limited to accelleration within 360 degrees.

Accordingly it is the object of the present invention to provide an apparatus and method which will make possible an angiographic scan of a human vascular portion though a wide angle during the short period that an acceptably safe injection of contrast medium remains in the portion.

SUMMARY OF THE INVENTION

According to the invention apparatus in an X-ray system for angiographic examination of a patient comprises a rotatable support; a motor for turning the support about a central axis; radiation means including an X-ray source for exposing a portion of a patient on the central axis, and an X-ray receptor generating video signals representing an image of the exposed patient volume, the source and receptor being aligned on a common radiation axis through and isocenter on the central axis; means on the rotatable support mounting the source and receptor at opposite sides of the central axis; and a programmer controlling the motor and the radiation means; wherein the X-ray source radiates a cone-shaped beam through a three-dimensional volume of the patient; the receptor generates a two-dimensional video image signal; and the programmer include a timer energizing the X-ray source at a continuous succession of predetermined angular positions of the rotating support and radiation axis while the patient is stationary, so as to produce a plurality of two-dimensional images of the patient volume at successive angles.

Further the invention involves a method of angiographic examination of a patient comprising disposing a vascular volume of a stationary patient on the radiation axis of a beam of conical X-rays rotating around a central axis through the patient; injecting a unit of X-ray contrast medium into the patient volume while the X-ray beam is rotating; energizing the X-ray beam in a scan of a continuous succession of rotational angles of the radiation axis to expose the patient while stationary and the single unit of contrast medium remains in the volume; and generating video signals representing the patient exposure.

DRAWING

The single drawing FIGURE is an end elevation of a rotary X-ray scanning apparatus according to the invention, shown partly in section, and with diagrammatic electrical wiring to a data processing programmer.

DESCRIPTION

As shown in the drawing, rotary X-ray apparatus is mounted on a floor base 1 from which a two-armed cradle 2 extends upwardly. At the upper end of each cradle arm is a rotary bearing 3 holding a circular gimbal 4 which may turn through a limited angle around a tilt axis A1. The gimbal carries four rollers 6 which rotatively support a large, hollow inner ring 7, the ring being driven by a motor M having a pulley 8 for a belt 9, as shown and described in detail in U.S. Pat. No. 4,426,725. The inner ring rotates continuously and repeatedly through 360 degrees about a central axis A2. The hollow interior space 11 of the inner ring 7 is closed by an outer circular wall 12, end walls 13 of which one is visible, and an X-ray transparent inner circular wall 14 around a central opening 16. The central opening admits a patient P lengthwise on a table T along the central axis A2. Attached to the patient are a cardiographic electrode 17 and a catheter 18 with a motorized pump 19 for injecting a contrast medium in to a selected vascular portion of the patient under examination.

Within the hollow ring 7 are an X-ray tube X and an image intensifier I located on a radiation axis A3 which intersects the rotational axis A2 of the ring and the tilt axis A1 of the gimbal at an isocenter C within the patient. The X-ray tube X has a high voltage anode K and a grounded anode A. The tube is of a known high power type (e.g. 15 kilowatts) having a focal spot of about 0.3 to 0.5 millimeters on a high speed rotating anode from which X-rays are radiated in a cone shaped beam along the radiation axis to the image intensifier I. Typically the distance from the anode to the image intensifier is 40 inches, and to the isocenter is 20 inches. This allows an image intensifier with a 7 or 8 inch on-axis field of view and an image of 512 or 1024 pixels squared, yielding a high detail resolution and a 2:1 enlargement. By tilting the gimbal 4 the fore and aft angle of the radiation axis through the patient may be adjusted.

Operation of the system is controlled by a computer or programmer 21 with a three-phase voltage supply 22. The programmer comprises a timer 23 which receives heart pulse signals from the electrode 17 attached to the patient P and starts the inner ring drive motor M. After allowing time for the motor to bring the inner ring to desired speed, or when otherwise programmed, the timer energizes the catheter injecting contrast medium into a vascular portion of the patient. The timer then immediately triggers the high voltage supply 24 for the X-ray tube causing the supply to apply a series of high voltage pulses to the tube so that it emits a series of very short X-ray bursts through the patient to the image intensifier I. The high voltage supply is connected to the X-ray tube through the sliding contacts of brushes or slip rings 15. Similarly slip rings conduct the video signals generated by the image intensifier in response to the X-ray bursts to a processing section 26 of the programmer. The processed video signals are saved in a storage memory 27 for transmission to a video display 28 or recorder 29 as selected by the examining physician.

The X-ray tube is of the strobe type, capable of using very high power, eg. 15 to 50 kilovolt, high voltage pulses of short duration, e.g. 0.008 to 0.010 seconds. Its rotating anode has a focal point of close to 0.03 millimeter diameter, and emits a cone shaped beam which forms a two-dimensional image at the image intensifier.

(This is to be contrasted with the fan shaped beam and one dimensional, line image of a computer assisted (CAT) scanner). After the timer 23 initiates injection of contrast medium into the patient it will stay within the vascular portion of the patient under examination only about three seconds. During these three seconds the motor M has a speed to rotate the inner ring 90 to 180 degrees and is of the vector or synchro type whose phase angle or position is controlled by the timer 23. The timer also controls the pulse rate of the high voltage supply 24 so that it supplies a short burst of X-rays at a preselected angle of the radiation axis A3 relative to the patient. Preferably ninety 8 to 10 millisecond X-ray pulses are emitted at thirty pulses per second during the three second rotation by the inner ring through 90 to 180 degrees of angle.

Surprisingly such rapid movement of the X-ray beam does not increase blurring of the intensifier image or its video signals beyond the unavoidable penumbra inherent in the X-ray shadow on the image intensifier. The unexpectedly clear image of 90 to 180 frames of video signals per 3 second scan of the radiation axis can be enhanced by making one scan before contrast medium injection, and, by a known data process subtracting that background image of the patient from the subsequent images after contrast medium injection. Moreover successive pairs of images provide a three-dimensional viewing of the patient.

It should be understood that the present disclosure is for the purpose of illustration only, and that the invention includes all modifications and equivalents falling within the appended claims.

I claim:

1. In an X-ray system for angiographic examination of a a selected volume within a patient, apparatus comprising:
   a support continuously rotatable around the volume;
   a motor for turning the support continuously about a central axis through the volume;
   radiation means including an X-ray source for exposing the selected volume of a patient on the central axis with an X-ray beam, and an X-ray receptor generating video signals representing an image of the selected patient volume, the source and receptor being aligned on a common radiation axis through an isocenter on the central axis;
   means on the rotatable support mounting the source and receptor at opposite sides of the central axis; and
   a programmer controlling the motor and the radiation means; wherein:
   the receptor generates a two-dimensional video image signal;
   and the programmer includes a timer means generating a series of timing pulses, and means connecting the timer means to the X-ray source for controlling the X-ray pulse rate of the X-ray source and energizing the X-ray source at a continuous succession of predetermined angular positions of the rotating support and radiation axis while the patient is stationary, so as to produce a plurality of two-dimensional images of the selected volume at continuously changing successive angles.

2. Apparatus according to claim 1 including motorized means for injection of a contrast medium into the patient wherein the programmer times energization of the injection means to occur while the support is rotating.

3. Apparatus according to claim 2 wherein the X-ray source is repeatedly energized while the contrast medium is in the patient volume being examined.

4. Apparatus according to claim 2 wherein the X-ray source is repeatedly energized while the support rotates through a substantial angle.

5. Apparatus according to claim 1 wherein the rotatable support is mounted within a gimbal on a rotative axis normal to the central axis.

6. Apparatus according to claim 1 wherein the X-ray source and receptor are electrically connected to the programmer by brushes on the rotatable support.

7. Apparatus according to claim 1 wherein the support is free to rotate repeatedly through 360 degrees.

8. Apparatus according to claim 7 including a 360 degree track allowing continuous rotation of the rotating support through successive 360 degree revolutions.

9. An X-ray system for angiographic examination of a selected volume within a patient comprising:
   a support rotatable around the selected volume;
   a motor for turning the support about a central axis through the selected volume;
   radiation means including an X-ray source for exposing the selected volume, and an X-ray receptor generating two-dimensional video signals representing an image of the selected volume;
   means on the rotatable support mounting the source and receptor at opposite ends of the central axis; and
   a programmer controlling the radiation means and the motor;
   wherein the programmer includes a timer with first means transmitting a start signal to the motor to initiate and maintain a continuous rotation of the support and radiation means through a substantial angle about the selected volume, and second means for generating a continuous series of timing pulses applied to the X-ray source during the continuous rotation, so as to expose the selected volume and produce a plurality of two-dimensional images of the selected patient volume from successive, continuously changing angles.

10. A method of angiographic examination of a selected volume of a patient comprising:
    disposing a selected volume of a stationary patient on the radiation axis of a beam of X-rays continuously rotating around a central axis through the patient;
    injecting a unit of X-ray contrast medium into the patient while the X-ray beam is rotating;
    generating a series of timing pulses and controlling the energization of the X-ray source at the timing pulse rate during a scan of a continuous succession of rotational angles of the radiation axis while the patient is stationary and the single unit of contrast medium remains in the volume; and
    generating video signals representing the patient exposure.

11. The method according to claim 10 including the steps of energizing the X-ray beam for a scan prior to injecting the contrast medium, generating video signals representing the prior scan, and subtracting the video signals of the prior scan from the subsequent scan with contrast medium.

12. The method according to claim 10 wherein the X-ray beam is continuously rotated through 360 degrees around the patient.

13. A method of angiographic examination of a selected volume within a patient comprising:

disposing the selected patient volume on a radiation axis of an X-ray source;

continuously rotating the radiation axis through a substantial angle about an axis through the selected volume;

injecting a unit of X-ray contrast medium into the patient volume;

generating a series of timing pulses causing the radiation source to expose the selected volume repeatedly during the continuous rotation while the single unit of contrast medium remains in the selected volume; and generating video signals representing the repeated exposures of the selected volume, so as to produce a plurality of two-dimensional images of the selected volume from successive, continuously changing angles.

* * * * *

REEXAMINATION CERTIFICATE (3309th)
United States Patent [19]
Grady

[11] B1 5,408,521
[45] Certificate Issued  Aug. 26, 1997

[54] ANGIOGRAPHIC X-RAY SYSTEM WIH 360 DEGREE SCANNING

[76] Inventor: John K. Grady, XRE Corporation, 300 Foster St., Littleton, Mass. 01460

Reexamination Request:
No. 90/004,269, Jun. 10, 1996

Reexamination Certificate for:
Patent No.: 5,408,521
Issued: Apr. 18, 1995
Appl. No.: 868,481
Filed: Apr. 14, 1992

[51] Int. Cl.$^6$ ............................................. H05G 1/64
[52] U.S. Cl. ........................... 378/96; 378/4; 378/15; 378/901
[58] Field of Search ................... 378/4, 8, 9, 13, 378/14, 15, 17, 19, 20, 95, 96, 98.2, 98.11, 98.12, 62, 901

[56] References Cited

U.S. PATENT DOCUMENTS

| | | |
|---|---|---|
| 4,382,184 | 5/1983 | Wernikoff . |
| 4,433,380 | 2/1984 | Abele et al. . |
| 4,672,651 | 6/1987 | Horiba et al. . |
| 4,995,064 | 2/1991 | Wilson et al. . |
| 5,034,987 | 7/1991 | Fujimoto et al. . |
| 5,093,850 | 3/1992 | Dinwiddie et al. . |
| 5,095,501 | 3/1992 | Kobayashi . |

FOREIGN PATENT DOCUMENTS 63-103609  7/1988  Japan .

OTHER PUBLICATIONS

"Coronary angiographic examination with the dynamic spatial reconstructor," *Circulation*, vol. 70, No. 2, Aug. 1984, pp. 209–216 (Block et al.).

"Physics and Technical Considerations in the Design of the DSR: A High Temporal Resolution Volume Scanner," *American Journal of Roentgenology*, vol. 134, Feb. 1980, pp. 369–374 (Ritman et al.).

"High–Speed Three–Dimensional X–Ray Computed Tomography: The Dynamic Spatial Reconstructor," *Proceedings of the IEEE*, vol. 71, No. 3, Mar. 1983, pp. 308–319 (Robb et al.).

"352. Rotational Stero–Digital Angiography," 1990, p. 1323 (Akasaka et al.).

*Primary Examiner*—David P. Parta

[57] ABSTRACT

An X-ray system scans the vascular portion of a human patient by a series of rapidly pulsed exposures from an X-ray tube rotated continuously through 360 degrees around the patient. The tube emits a cone-shaped beam through the patient to a receptor which generates a corresponding series of two-dimensional video images of the patient from successive angles.

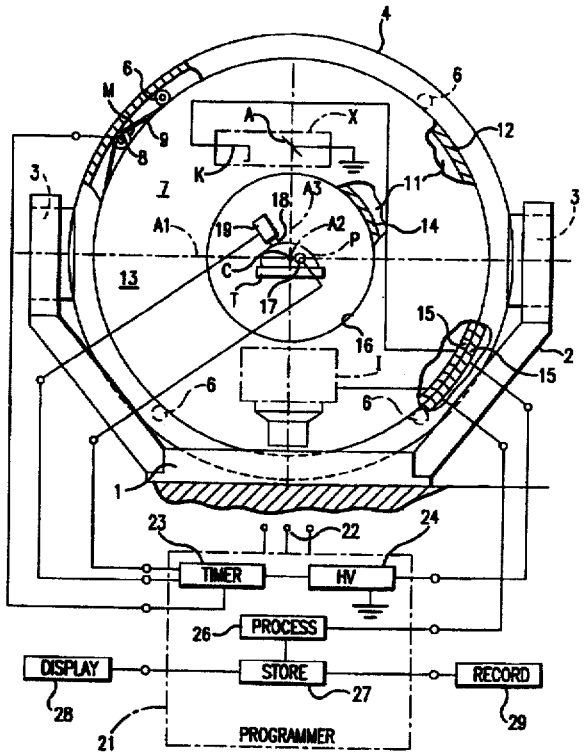

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 6 and 9 are cancelled.

Claims 1, 10 and 13 are determined to be patentable as amended.

Claims 2–5, 7, 8 and 11–12, dependent on an amended claim, are determined to be patentable.

New claims 14–18 are added and determined to be patentable.

1. In an X-ray system for angiographic examination of a selected volume within a patient, apparatus comprising:
   a support continuously rotatable around the volume;
   a motor for turning the support continuously about a central axis through the volume;
   radiation means including an X-ray source for exposing the selected volume of a patient on the central axis with an X-ray beam, and an X-ray receptor generating video signals representing an image of the selected patient volume, the source and receptor being aligned on a common radiation axis through an isocenter on the central axis;
   means on the rotatable support mounting the source and receptor at opposite sides of the central axis; and
   a programer controlling the motor and the radiation means; wherein:
   the receptor generates a two-dimensional video image signal; and the programmer includes a timer means generating a series of timing pulses, and means connecting the timer means to the X-ray source for controlling the [X-ray pulse rate of the] X-ray source *to emit X-rays with a pulse duration of eight to ten milliseconds* and energizing the X-ray source at a continuous succession of predetermined angular positions of the rotating support and radiation axis while the patient is stationary, so as to produce a plurality of two-dimensional images of the selected volume at continuously changing successive angles.

10. A method of angiographic examination of a a selected volume of a patient comprising: disposing a selected volume of a stationary patient on the radiation axis of a beam of X-rays continuously rotating around a central axis through the patient;
   injecting a unit of X-ray contrast medium into the patient while the X-ray beam is rotating;
   generating a series of timing pulses and controlling the energization of the X-ray source [at the timing pulse rate] *to emit X-rays with a pulse duration of eight to ten milliseconds* during a a scan of a continuous succession of rotational angles of the radiation axis while the patient is stationary and the single unit of contrast medium remains in the volume; and generating video signals representing the patient exposure.

13. A method of angiographic examination of a selected volume within a patient comprising:
   disposing the selected patient volume on a radiation axis of an X-ray source;
   continuously rotating the radiation axis through a substantial angle about an axis through the selected volume;
   injecting a unit of X-ray contrast medium into the patient volume;
   generating a series of timing pulses causing the radiation source to *emit X-rays with a pulse duration of eight to ten milliseconds so as to* expose the selected volume repeatedly during the continuous rotation while the single unit of contrast medium remains in the selected volume; and
   generating video signals representing the repeated exposures of the selected volume, so as to produce a purality of two-dimensional images of the selected volume from successive, continuously changing angles.

*14. In an X-ray system for angiographic examination of a selected volume within a patient, apparatus comprising:*
   *a support continuously rotatable around the volume;*
   *a motor for turning the support continuously about a central axis through the volume;*
   *radiation means including an X-ray source for exposing the selected volume of a patient on the central axis with an X-ray beam, and an X-ray receptor generating video signals representing an image of the selected patient volume, the source and receptor being aligned on a common radiation axis through an isocenter on the central axis;*
   *means on the rotatable support mounting the source and receptor at opposite sides of the central axis;*
   *means for mounting the support to tilt about an axis intersecting the central axis so as to adjust the angle of the radiation axis to the selected volume,*
   *a programmer controlling the motor and the radiation means; wherein:*
   *the receptor generates a two-dimensional video image signal; and the programmer includes a timer means generating a series of timing pulses, and means connecting the timer means to the X-ray source for controlling the X-ray pulse rate of the X-ray source and energizing the X-ray source at a continuous succession of predetermined angular positions of the rotating support and radiation axis while the patient is stationary, so as to produce a plurality of two-dimensional images of the selected volume at continuously changing successive angles.*

*15. In an X-ray system for angiographic examination of a selected volume within a patient, apparatus comprising:*
   *a support continuously rotatable around the volume;*
   *a motor for turning the support continuously about a central axis through the volume;*
   *radiation means including an X-ray source for exposing the selected volume of a patient on the central axis with an X-ray beam, and an X-ray receptor generating video signals representing an image of the selected patient volume, the source and receptor being aligned on a common radiation axis through an isocenter on the central axis;*
   *means on the rotatable support mounting the source and receptor at opposite sides of the central axis; and* a programmer controlling the motor and the radiation means; wherein:

the receptor generates a two-dimensional video image signal; and the programmer includes a timer means generating a series of timing pulses, and means connecting the timer means to the X-ray source for controlling the X-ray pulse rate of the X-ray source to provide ninety pulses each eight to ten milliseconds in duration at the rate of thirty pulses per second and energizing the X-ray source at a continuous succession of predetermined angular positions of the rotating support and radiation axis through ninety to one hundred eighty degrees while the patient is stationary, so as to produce a plurality of two-dimensional images of the selected volume at continuously changing successive angles.

16. The method according to claim 10 further characterised in that the timing pulses energize the X-ray source for pulse durations of eight to ten milliseconds.

17. The method according to claim 10 further characterized in that the timing pulses energize the X-ray source for pulse durations of eight to ten milliseconds during rotation of the radiation axis at thirty to sixty degrees per second.

18. The method of angiographic examination of a patient volume which comprises;

disposing a selected volume of a stationary patient on the radiation axis of a beam of X-rays continuously rotating about a central axis through the patient;

injecting the unit of X-ray contrast medium into the patient while the X-ray beam is rotating;

irradiating the patient with X-rays on the radiation axis rotating around the patient;

pulsing the X-rays for a duration of eight to ten milliseconds while the radiation axis rotates at a rate of thirty to sixty degrees per second; and generating video signals representative of the patient volume exposed to each pulse of radiation.

* * * * *